United States Patent [19]

Kimura et al.

[11] Patent Number: 5,650,495
[45] Date of Patent: Jul. 22, 1997

[54] PROTEIN HAVING AN AFFINITY FOR A HEPARIN-BINDING GROWTH FACTOR

[75] Inventors: Michio Kimura, Sakado; Kazuyuki Doi, Tokyo, both of Japan

[73] Assignee: Hoechst Japan Limited, Tokyo, Japan

[21] Appl. No.: 549,752

[22] PCT Filed: May 25, 1994

[86] PCT No.: PCT/JP94/00832

§ 371 Date: Mar. 5, 1996

§ 102(e) Date: Mar. 5, 1996

[87] PCT Pub. No.: WO94/28022

PCT Pub. Date: Dec. 8, 1994

[30] Foreign Application Priority Data

May 26, 1993 [JP] Japan .................................. 5-213813

[51] Int. Cl.⁶ .......................... C07K 14/475; C07K 14/51
[52] U.S. Cl. ...................... 530/399; 530/350; 930/120
[58] Field of Search .................... 530/350, 399; 930/120

[56] References Cited

PUBLICATIONS

Gieffers et al., Eur. J. Cell Biol. 62 (2): 352–361 (1993).
Katoh et al., Cancer Res. 53 (5): 1136–1141 (1993).
Kuo et al., J. Biol. Chem. 265 (31): 18749–18752 (1990).
Experimental Medicine 10 (1): 25–31 (1992).
Raulo et al. J. Biol. Chem. 267 (1992) 11408–11416.

*Primary Examiner*—Lora M. Green
*Assistant Examiner*—Robert C. Hayes
*Attorney, Agent, or Firm*—Finnegan, Henderson, Farabow, Garrett & Dunner, L.L.P.

[57] ABSTRACT

An isolated protein having the amino terminal sequence of SEQ ID No. 1 and having a molecular weight of about 200 KDa is described. This animal brain-derived protein binds to OSF-1 (HBGF-8), which is a heparin-binding growth factor that has neuronal differentiation-enhancing activity, and a proliferative action on osteoblasts.

8 Claims, 3 Drawing Sheets

PROTEIN HAVING AN AFFINITY FOR A HEPARIN-BINDING GROWTH FACTOR

TECHNICAL FIELD

This invention relates to a novel protein, more particularly, to an animal brain derived protein having an avidity with a heparin-binding growth factor.

TECHNICAL BACKGROUND

Recently, many growth factors have been isolated from various animal tissues and animal cells, and their characters have been elucidated. Among these growth factors is known a group of proteins called heparin-binding growth factors (HBGFs) having a high affinity with heparin. Among the most widely known HBGFs, there are acidic fibroblast growth factors (aFGF) and basic fibroblast growth factors (bFGF) found in the 1930's. Among those found recently, OSF-1 (Japanese Patent Kokai No. 117398/1992) or HBGF-8 (Japanese Patent Kokai No. 159299/1992) can be cited. Although OSF-1 and HBGF-8 were found independently, they are the identical substance.

These proteins are known to have a differentiation-enhancing action to neuronal cells and proliferation-enhancing action to osteoblasts, and they are considered to be possibly involved in the diseases accompanied with decrease of nerve function and decrease of osteogenetic potency. Therefore, if factors that connect with those proteins and control the actions of those proteins are found, they are expected to be applied to therapeutics of neuronal function diseases and osteoblast potency diseases. However, reported until present is confined only to a part of such factors which connect with heparin-binding growth factors and control their action, such as FGF receptors for FGF, and a satisfactory result has not yet been obtained for the application of these factors to a therapeutic drug. Yet, there is still no report on any binding proteins for recently found OSF-1 (HBGF-8).

Then, the present inventors have attempted to find out a protein having an avidity to this factor, by focusing on OSF-1 (HBGF-8) among heparin-binding growth factors and finally completed this invention.

DISCLOSURE OF THE INVENTION

An object of the present invention is to provide a novel protein which is useful as a therapeutic drug for neuro-functional and osteogenetic diseases by finding out the proteins connecting with OSF-1, one of heparin-binding growth factors having a differentiation-enhancing action to neuronal cells and proliferation-enhancing action to osteoblasts, and controlling these actions.

The present inventors paid their attention to the fact that OSF-1 exists abundantly in animal brains, and have attempted to isolate proteins having an avidity with OSF-1 from brains, based on a hypothesis that the proteins which connect with OSF-1 should exist also in brains. Namely, the present inventors thought it possible to isolate OSF-1 and the proteins having an avidity with it from brains in the state as they are binding, by isolating OSF-1 from brains under a mild condition. The present inventors thought it also possible to isolate, thereafter, an OSF-1 binding protein by releasing the bondage of OSF-1 and desired protein. These have been proved by experiments, which led to the completion of the present invention.

The brains from juvenile rats of 14 days after birth was used because it was anticipated that such brains especially had larger amount of various growth factors with high activity. The brains were purified until OSF-1-binding proteins were made homogeneous by using centrifugation, ion-exchange column chromatography and reverse phase column chromatography. Thereafter, sequencing of amino terminal sequence of the protein was carried out to find out that the protein provided in the present invention is an entirely novel protein, and it was named HBP-200.

The protein provided in the present invention is a novel protein isolated from animal brains, having the following physical properties and amino terminal sequence;

(1) Molecular weight: About 200 KDa (by SDS-PAGE method under reducing condition)

(2) Amino terminal sequence: Amino acid sequence shown in SEQ ID No.: 1 of the Sequence Listing (3) Character: Having an avidity with OSF-1 (HBGF-8)

Furthermore, the proteins provided in the present invention can be isolated also from bone tissues, osteoblasts, osteoblast strains, fibroblasts and fibroblast strains in which OSF-1 (HBGF-8) is known to exist.

EXAMPLE

Figure 1:
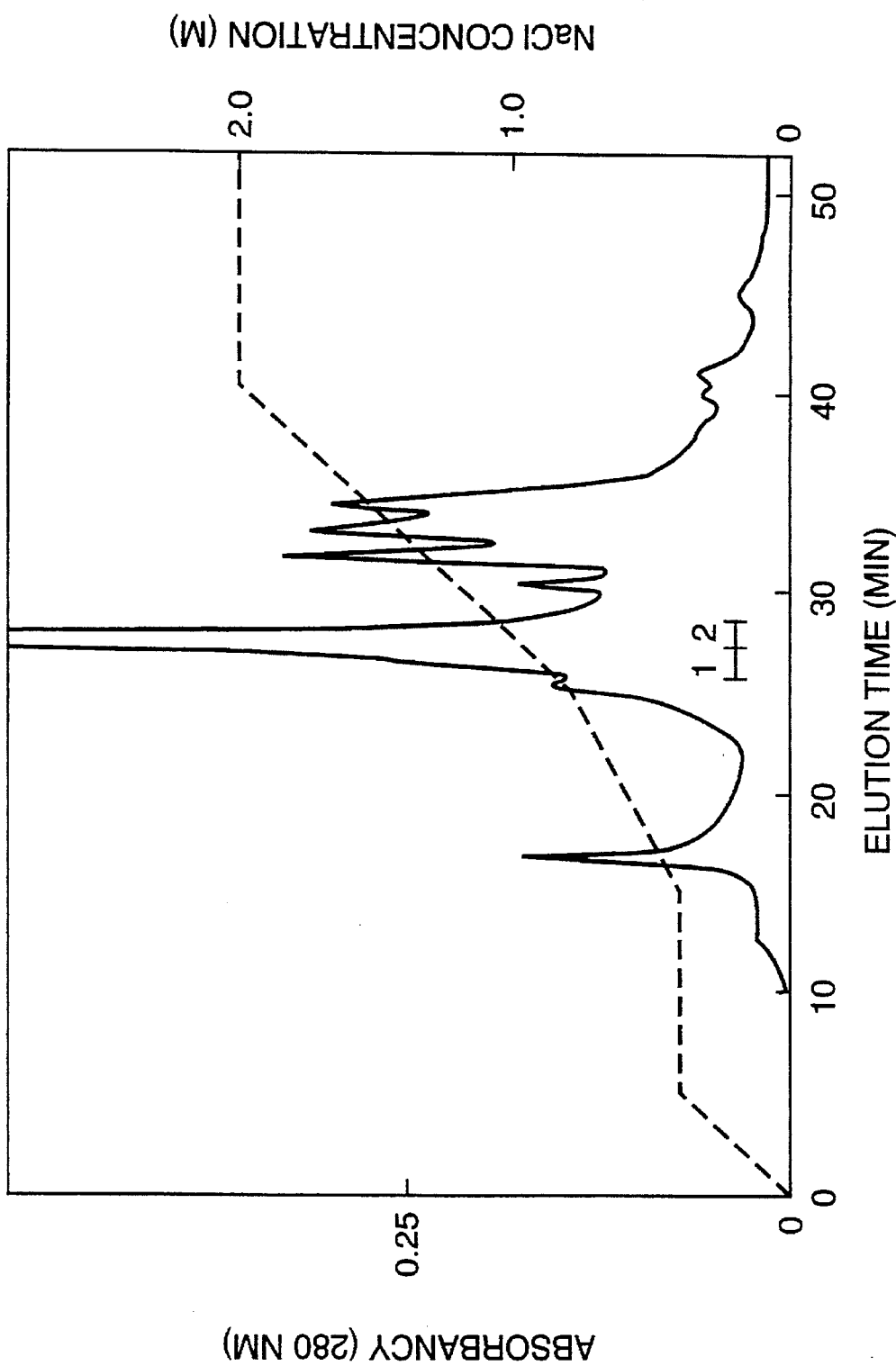
FIG. 1 shows an elution pattern from CM-column chromatography. A solid line shows the absorbance at 280 nm, while a dotted line shows NaCl concentration.

The following examples are intended to further illustrate the invention and are not to be construed to limit the invention.

Example 1

Purification of HBP-200

(1) Purification by Centrifugal Method

The brains of juvenile rats of 14 days after birth were collected and cryopreserved (after freezing with liquid nitrogen, preserved at −60° C.) until processed for purification. 100 g of frozen brains of rats were used for purification. They were firstly blended 3 times in 300 ml of a tissue blend buffer (20 mM Tris-HCl, pH 7.2, 1 mM PMSF, 5 mM EDTA) for 30 seconds by homogenizer. Then, this blended solution was centrifuged for 1 hour with 150,000× g and obtained a centrifuged precipitate. This centrifuged precipitate was washed with tissue blend buffer, and centrifuged again for 1 hour with 150,000× g.

The precipitate thus obtained was solubilized with solubilizing buffer (50 mM Tris-HCl, pH 8.5, 50 mM NaCl, 50 mM octylglucoside, 1 mM PMSF, 5 mM EDTA) 300 ml, and the solution was centrifuged for 1 hour with 150,000× g. This centrifuged precipitate was again solubilized with the solubilizing buffer, centrifuged for 1 hour with 150,000× g, and the 2 supernatants of these centrifugations were mixed for use for the following column developments.

(2) Purification by Affinity Column Chromatography

The centrifuged supernatant obtained in the above (1) was applied to Heparin Sepharose Column (1.6 cm diameter×15 cm length, Pharmacia AB, Sweden) which had been equilibrated with heparin column buffer (50 mM Tris-HCl, pH 8.5, 50 mM NaCl, 5 mM octylglucoside) and washed with the column buffer. Then, after washing with the buffer containing 0.5M NaCl, the proteins adsorbed on the column was eluted with linear gradient of the buffer containing NaCl of 0.5M to 2.5M.

(3) Purification by Ion-Exchange Column Chromatography

An electrophores was carried out by using a part of the each eluted fraction. The fractions containing OSF-1 were confirmed, collected and pooled. The pooled solution was diluted into 2 times with CM column buffer (20 mM phosphoric acid buffer, pH 6.5), applied to CM-HPLC column (8.2 mm diameter×75 mm length, Waters, USA) equilibrated with the same buffer and washed with CM column buffer. Then, the column was eluted with linear gradient of the same buffer containing NaCl. Elution pattern is shown in FIG. 1.

The eluted main fractions 1 and 2 were collected and pooled. The pooled solution was used for the following column developments.

(4) Purification by Reverse Phase Column Chromatography

Figure 2:
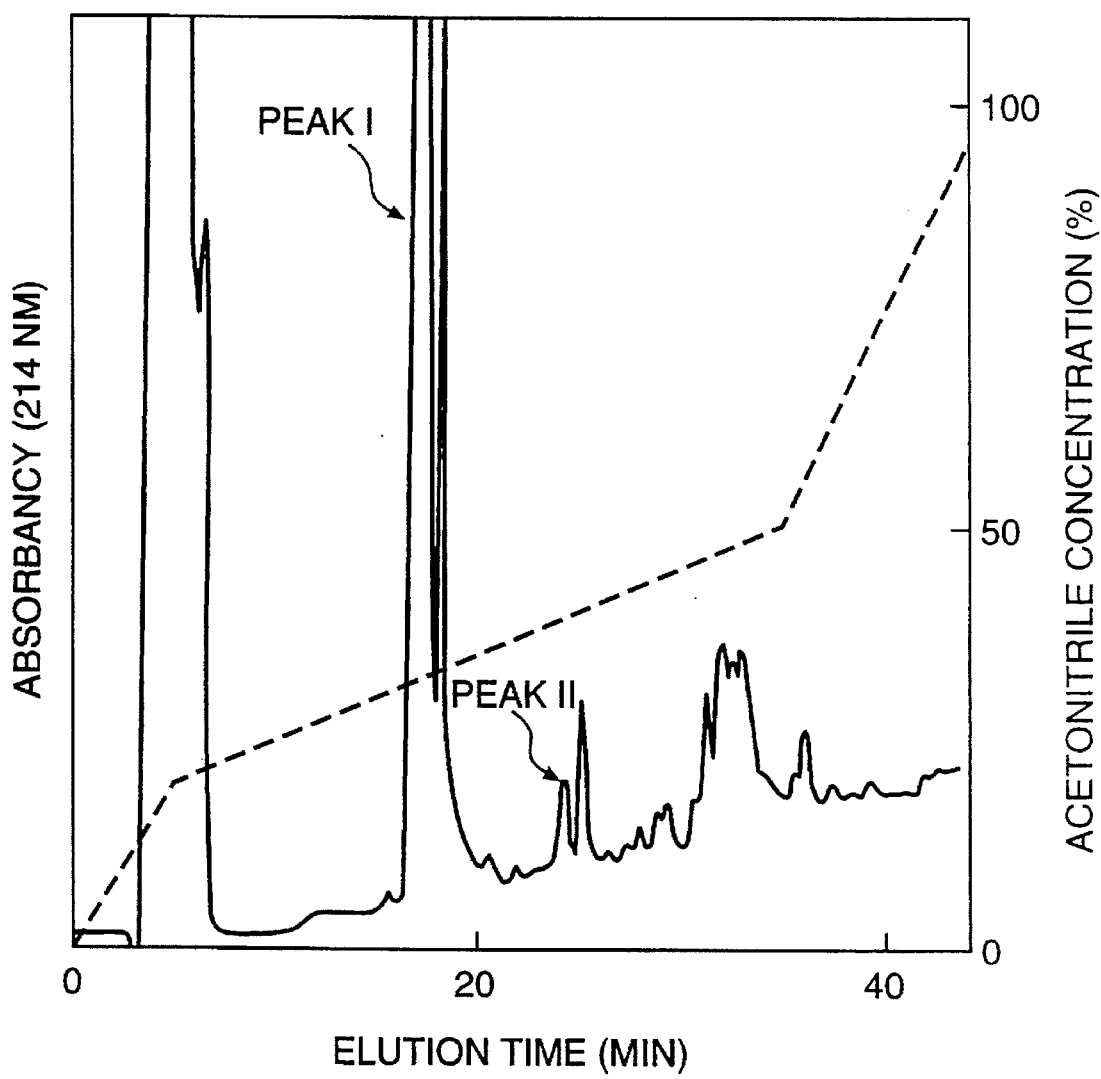
FIG. 2 shows an elution pattern by reverse phase HPLC. A solid line shows the absorbance at 214 nm, while a dotted line shows acetonitrile concentration. Peak I in the drawing shows the peak of OSF-1, while peak II shows the peak of HBP-200.
Figure 3:
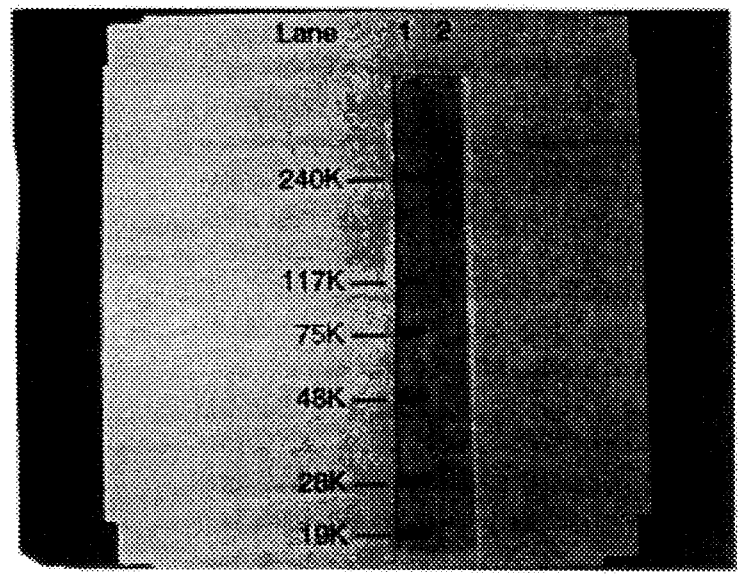
FIG. 3 shows a migration pattern of SDS-PAGE under reducing condition of the peak II (HBP-200) isolated by reverse phase HPLC. Lane 1 shows molecular weight markers, while lane 2 shows a migration pattern of the peak II.

The solution obtained in the above (3) was further purified by reverse phase HPLC and the desired protein binding with OSF-1 was isolated and macerated from OSF-1. Namely, the solution obtained in the above (3) was applied to the hydrophobic column: Cosmosil 5C4-300 (4.6 mm diameter× 250 mm length, Nacalai Tesque Inc., Japan) equilibrated with water containing 0.05% TFA, and eluted with linear gradient by acetonitrile. The elution pattern is shown in FIG. 2. It was confirmed that peak I is OSF-1 by SDS-PAGE, amino acid analysis and other analytical methods.

The peak II was analyzed by SDS-PAGE under reducing condition to obtain a single protein showing a molecular weight of about 200 KDa. The final yield of the protein was about 10 μg.

Example 2

Amino acid sequencing of HBP-200

Amino acid terminal sequence of HBP-200 was determined by auto N-terminal amino acid sequencer (Applied Bio System, Model 477A, USA). The amino acid sequence is shown in SEQ ID No.: 1 of the Sequence Listing.

Field of Industrial Application

HBP-200 obtained in the present invention is a useful novel protein as a therapeutic drug for disorders of nerve function and osteogenetic potency because the protein connects with OSF-1 (HBGF-8), one of heparin-binding growth factors having a differentiation-enhancing action to neuronal cells and a proliferation action to osteoblasts, and controls these actions.

We claim:

1. An isolated protein having the amino terminal sequence of SEQ ID No. 1 and having a molecular weight of about 200 KDa by SDS-PAGE analysis under reducing conditions.

2. The protein according to claim 1 which is isolated from animal brains.

3. The protein according to claim 1 which binds to heparin-binding growth factors.

4. The protein according to claim 3 in which the heparin-binding growth factor is osteoblast-specific factor-1 (OSF-1).

5. The protein according to claim 2 which is isolated from rat brain.

6. The protein according to claim 1 which is isolated from bone tissues.

7. The protein according to claim 1 which is isolated from osteoblasts.

8. The protein according to claim 1 which is isolated from fibroblasts.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Rattus norvegicus
        ( B ) STRAIN: Sprague-Dawley
        ( F ) TISSUE TYPE: Cerebral Tissue ( x i ) SEQUENCE DESCRIPTION: SEQ ID NO:1:

```
Ser  Lys  Thr  Glu  Gly  Pro  Asn  Lys  Glu  Leu  Glu  Lys  Glu  Gly  Pro  Lys
1                  5                            10                          15

Ala  Val  Lys  Asp  Pro  Val  Ala  Val  Glu  Leu  Ile  Lys
                20                           25
```